(12) United States Patent
Kim et al.

(10) Patent No.: US 8,193,245 B2
(45) Date of Patent: Jun. 5, 2012

(54) COMPOSITION COMPRISING OLEIC ACID AND THE USE THEREOF

(75) Inventors: Hocheol Kim, Seoul (KR); Dae Hee Lee, Seoul (KR); Mi Yeong Kim, Seoul (KR); Young Min Boo, Seoul (KR); Ni Na Ha, Incheon (KR); Jin Hee Jung, Seoul (KR)

(73) Assignee: University-Industry Cooperation Group of Kyung Hee University, Yongin-si, Gyeonggi-do (KR)

( * ) Notice: Subject to any disclaimer, the term of this patent is extended or adjusted under 35 U.S.C. 154(b) by 505 days.

(21) Appl. No.: 12/064,134

(22) PCT Filed: Jan. 9, 2006

(86) PCT No.: PCT/KR2006/000082
§ 371 (c)(1),
(2), (4) Date: Feb. 19, 2008

(87) PCT Pub. No.: WO2007/021061
PCT Pub. Date: Feb. 22, 2007

(65) Prior Publication Data
US 2008/0227860 A1 Sep. 18, 2008

(30) Foreign Application Priority Data
Aug. 19, 2005 (KR) .................. 10-2005-0076324

(51) Int. Cl.
*A61K 31/20* (2006.01)
(52) U.S. Cl. ......... 514/560; 514/17.7; 514/18.1; 514/42

(58) Field of Classification Search .............. 514/560, 514/17.7, 18.1, 42
See application file for complete search history.

(56) References Cited

OTHER PUBLICATIONS

Kevin Sheth, . Review of Huntington's disease , 2005 (Retrieved from the internet on Feb. 6, 2010, URL: http://healthguide.howstuffworks.com/huntingtons-disease-ictionary.htm/printable.*
Sztriha et al. (Brain Research, 550 (1991) 257-262.*
Battino et al., Public Health Nutrition, 2004, vol. 7 (7), 953-958.*
Tacconi et al, Neurochemical Research, 1998, vol. 23 (5) pp. 759-765.*
Filik et al., European Journal of Clinical Nutrition, 2003, vol. 57, p. 191.*
Leader article,2000, Retrieved from the internet on May 14, 2010, html-http://www.ion.ac.uk/archives/170_parkinsons_importance_of nutritional_support.html.*
Rodriguez-Rodriguez et al., "The neurotrophic effect of oleic acid includes dendritic differentiation and the expression of the neuronal basic helix-loop-helix transcription factor NeuroD2", J. Neurochem Mar. 2004, vol. 88(5), pp. 1041-1051.

(Continued)

*Primary Examiner* — Savitha Rao
(74) *Attorney, Agent, or Firm* — Lucas & Mercanti LLP

(57) ABSTRACT

The present invention relates to the pharmaceutical composition and health care food comprising oleic acid having neuroprotective activity. The oleic acid of the present invention has potent neuroprotective effect and recovery effect on neurological behavior. Therefore, it is useful as the therapeutics for the prevention or treatment of degenerative brain diseases in human or mammal.

2 Claims, 2 Drawing Sheets

A : Control , B: 1 mg/kg, C: 10 mg/kg, D: 100 mg/kg

OTHER PUBLICATIONS

Granda et al., "Oleic acid induces GAP-43 expression through a protein kinase C-mediated mechanism that is independent of NGF but synergistic with NT-3 and NT-415", Brain Res. 2003 vol. 988, pp. 1-8.

Velasco et al., "Role of oleic acid as a neurotrophic factor is supported in vivo by the expression of GAP-43 subsequent to the activation of SREBP-1 and the up-regulation of stearoyl-CoA desaturase during postnatal development of the brain", Brain Res. 2003, vol. 977, pp. 103-111.

Medina et al., "Astrocyte-synthesized oleic acid behaves as a neurotrophic factor for neurons", J. Physiol.—Paris, 2002, vol. 96, pp. 265-271.

* cited by examiner

[Fig. 1]
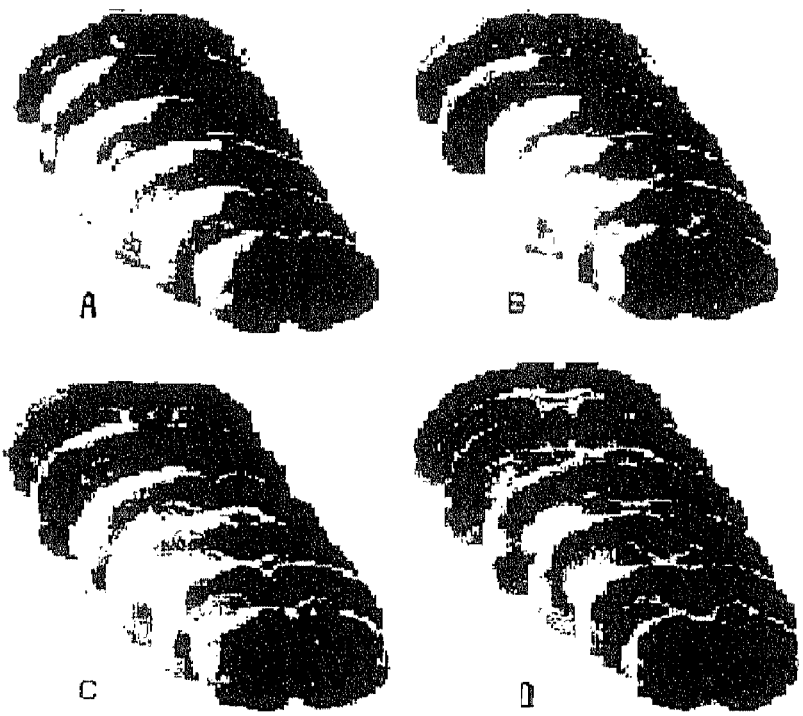
A: Control, B: 1 mg/kg, C: 10 mg/kg, D: 100 mg/kg
[Fig. 2]
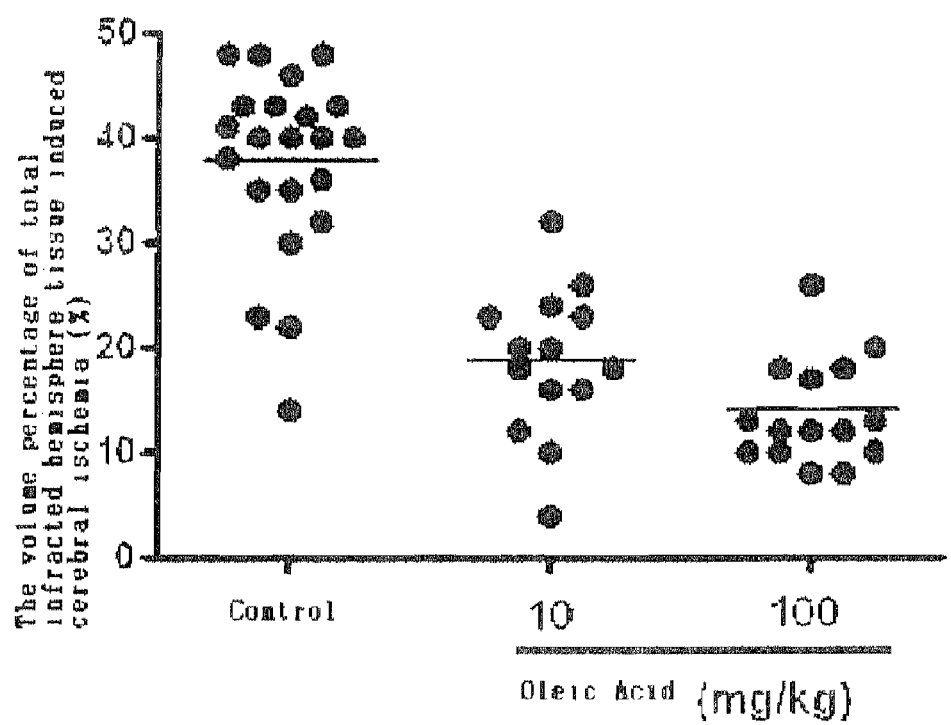

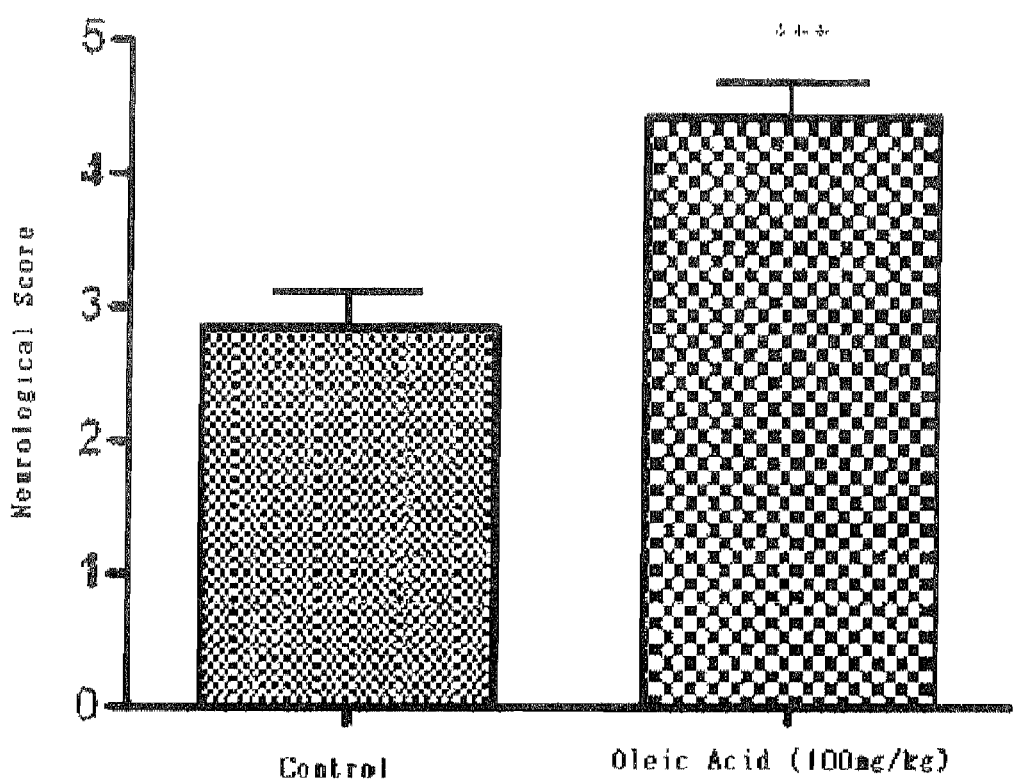
[Fig. 3]

COMPOSITION COMPRISING OLEIC ACID AND THE USE THEREOF

CROSS-REFERENCE TO RELATED APPLICATIONS

This application is a 371 of PCT/KR2006/000082 filed on Jan. 9, 2006, which claims the benefit of Korean Patent Application No. 10-2005-0076324 filed on Aug. 19, 2005, the contents of each of which are incorporated herein by reference.

TECHNICAL FIELD

The present invention relates to a composition comprising oleic acid having neuronal cell-protective activity

BACKGROUND ART

Since the aging society problem has paid attention recently, the interest on the character of aged peoples and the welfare of aged people such as accommodation, health, culture, leisure etc and the statistic demand thereon has been increased till now. The main cause of death in aging society is chronic degenerative disease not acute infectious diseases which has been the main cause of death long years ago. Especially, the cerebral ischemic disease among the chronic degenerative diseases is very important disease which was recorded as $2^{nd}$ among the simple causes of death.

Brain stroke is one of the major public health problem in degenerative disease and the mortality rate from stroke is surpassed only by that of heart. The two major categories of stroke are cerebral ischemia and hemorrhage. The former is caused by reduction of blood flow and the latter is caused by bleeding from brain vessels. Reduction of blood flow is occurred by an occlusion in a blood vessel by a blood clot or other things. Ischemic stroke accounts for 80% of all stroke It has been reported that the cause of damage of brain neuronal cells are the release of excessive excitational neurotransmitter, the production of free radical, the inhibition of protein synthesis, abnormal expression of gene and the activation of immune response etc., however, there has been not yet developed therapeutically effective agent to protect the damage of brain neuronal cells.

t-PA (tissue-plasminogen activator), a sole approved platelet agglutination inhibitor by FDA dissolve the blood agglutination which provides rapid supply of oxygen and glucose. Accordingly, since the drug could not protect neuronal cell directly, it require rapid use and gives rise to hemorrhagic stroke resulting from thinned blood wall in case of over-dose or long-term use because of its property. MK-801, a calcium channel blocker, to effectively inhibit initial calcium influx has been on clinical trial however it has been also dropped to develop further.

Accordingly, there have been needed to try seeking safe and potent natural resources which show treating and preventing effect on the brain diseases through authentic experiments till now.

Oleic acid, a unsaturated fatty acid existed in vivo shows M.W (282.5), m.p. (13.3° C.), b.p. (223° C./10 mmHg), and colorless and greasy liquid. In nature, it existed as main components of plant oils such as olive oil etc and animal oil such as the oil of cow and pig etc. The oil is reproduced from palmitic acid through stearic acid or transformed into linoleic acid in plant. It exists within cell membrane as a linked form with glycerol and ester (glyceride) rather than free form type therein. It has one double bond within one molecule and shows cis-type geometric isomer different from trans-type geometric isomer (elide acid).

There have been reported that it has the anticancer-effect (Menendez et al., Annals of Oncology, p 10, 2005), promotes the blood circulation by lowering blood viscosity (Alberts et al, Gerland Publishing, Inc., New York, 1994), the myelination and regeneration of neuronal cells (Medina and Tabernero, J. Physiology, 96, pp 265-271, 2002) till now.

However, there has been no disclosure or suggestion on the neuronal cell protecting activity of oleic acid, especially through animal model test for treating or inhibiting neuronal diseases such as brain stroke till now.

The inventors of the present invention have intensively carried out the scientific investigation concerning pharmacological effects and its mechanism of action of oleic acid. As a result of the investigation, the inventors have discovered that it shows novel pharmacological effects, especially, its preventing or treating activity for functional disorder of sensory neuron and they have finally completed the present invention.

DISCLOSURE OF INVENTION

Technical Problem

Accordingly, it is an object of the present invention to provide a pharmaceutical composition comprising oleic acid as an active ingredient in an amount effective to protect neuronal cell and to treat or prevent human or mammal suffering from brain diseases such as brain stroke and degenerative brain diseases, together with a pharmaceutically acceptable carrier.

Technical Solution

In accordance with the present invention, the present invention provides a pharmaceutical composition comprising oleic acid, as an active ingredient in an effective amount to protect neuronal cell.

Hereinafter, present invention shall be explained in detail as follows.

The oleic acid of the present invention is Cis-9-octadecenoic acid expressed by following chemical structure 1.

Chemistry Figure 1

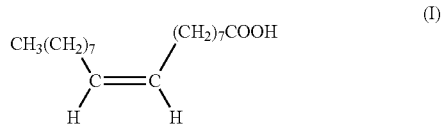

The term degenerative brain diseases disclosed herein comprise brain stroke, cerebral ischemia, Huntington's disease, Creutzfeld-Jakob disease, Alzheimer's disease (AD), Parkinson's disease (PD), senile dementia and the like.

Above described oleic acid can be obtained by the procedures as follows: oil material derived from plant or animal oil is pulverized to extract therefrom; the powder is extracted with hexane or chloroform solvent and the extract is concentrated to obtain concentrated non-polar solvent extract; the extract is subjected to silica gel column chromatography with solvent mixture (acetone: hexane) as a mobile phase to isolate purposed oleic acid.

The present invention provides a pharmaceutical composition comprising oleic acid prepared by the above-described method, as an active ingredient in an effective amount to protect neuronal cell and to treat or prevent human or mammal suffering from degenerative brain diseases such as brain stroke and cerebral ischemia, together with a pharmaceutically acceptable carrier.

The present invention also provides a use of oleic acid for the preparation of the medicament to prevent or treat degenerative brain disease such as brain stroke and cerebral ischemia of mammal or human.

Additionally, the present invention also provide a method of treating or preventing brain disease such as brain stroke and cerebral ischemia in a mammal comprising administrating to said mammal an effective amount of above described extract, together with a pharmaceutically acceptable carrier thereof.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the present invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection. Suitable examples of the carriers include physiological saline, polyethylene glycol, ethanol, vegetable oils, isopropyl myristate, etc., but are not limited to them. For topical administration, the extract of the present invention can be formulated in the form of ointments and creams.

Pharmaceutical formulations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract of the present invention varies depending on the condition and the weight of the subject, severity, drug form, route and period of administration, and may be chosen by those skilled in the art. However, in order to obtain desirable effects, it is generally recommended to administer at the amount ranging 0.01-10 g/kg, preferably, 1 to 5 g/kg by weight/day of the inventive extract. The dose may be administered in single or divided into several times per day. In terms of composition, the composition should be present between 0.01 to 80% by weight, preferably 0.5 to 50% by weight based on the total weight of the composition.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

The present inventors demonstrated that present composition comprising above described mulberry extract of the present invention have preventing or treating activity of brain stroke by accomplishing in vivo experiment already well known in the art, e.g., middle cerebral artery occlusion model test which is consisted of following step i.e., nylon filament is inserted into internal carotid artery to occlude middle cerebral artery and 120 minutes after, the filament is removed again to allow the reperfusion of the artery.

Accordingly, it is another object of the present invention to provide a health care food comprising the above-described oleic acid of the present invention prepared by above processes and a sitologically acceptable additive to protect neuronal cell and to prevent or improve brain diseases such as brain stroke and cerebral ischemia.

Above described composition therein can be added to food, additive or beverage for prevention of brain diseases such as brain stroke and cerebral ischemia as a form of tablet, capsule, pill or beverage type. For the purpose of preventing brain stroke diseases, wherein, the amount of above described compound of the present invention in food or beverage may generally range from about 0.1 to 15 w/w %, preferably 1 to 10 w/w % of total weight of food for the health food composition and 1 to 30 g, preferably 3 to 10 g on the ratio of 100□ of the health beverage composition.

Providing that the health beverage composition of present invention contains above described compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100□ of present beverage composition.

The other components rather than aforementioned composition are various nutrients, a vitamin, a mineral or an electrolyte, synthetic flavoring agent, a coloring agent and improving agent in case of cheese chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage etc. The other component rather than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition.

Examples of addable food comprising aforementioned compound therein are various food, beverage, gum, vitamin complex, health improving food and the like.

It will be apparent to those skilled in the art that various modifications and variations can be made in the compositions, use and preparations of the present invention without departing from the spirit or scope of the invention.

Advantageous Effects

The composition comprising oleic acid according to the present invention shows protective effect of neuronal cell and preventing or treating effect of brain stroke and cerebral ischemia. Therefore, it is useful in the prevention or treatment of degenerative brain diseases in human or mammal.

BRIEF DESCRIPTION OF THE DRAWINGS

The above and other objects, features and other advantages of the present invention will more clearly understood from the following detailed description taken in conjunction with the accompanying drawing, in which;

FIG. 1 shows the protective effect of various concentration of oleic acid on the injury of brain tissue using by TTC staining method, FIG. 2 represents the comparison of the effect of control using 5% Tween 20 and test group on brain tissue section of brain injury model, FIG. 3 presents the recovery activity of various concentration of oleic acid on the neuronal behavior.

BEST MODE FOR CARRYING OUT THE INVENTION

The present invention is specifically explained by the following examples. However, it should be understood that the present invention is not limited to these examples in any manner.

Reference Example 1

Preparation of Experiment

The procedure and experimental method used in Experimental Examples was described as follows:
Animal 8 weeks-old male Sprague-Dawley rats weighing about 300 g were procured from Samtaco Co. Ltd. (Seoul), fasted up providing with free access to water and feed and acclimated to experimental environment for 1 week.

Experimental Example 1

Neuroprotective Activity

To determine the neuronal cell protective effect on neuronal cell injury caused by focal cerebral ischemia, the modified intraluminal suture method disclosed in the literature (*Zea longa* et al, *Stroke* 20 pp 84-91, 1989) was performed as follows:

The rat was orally anesthetized with 5% isoflurane gas (mixed gas with the gas mixture consisting of 70% $N_2O$ and 30% $O_2$ gas and 5% isoflurane) and maintained with 5% isoflurane gas during experiment.

The skin at the center of rat neck was excised and right-handed CCA (common carotid artery) and ECA (external carotid artery) were isolated from neighboring tissue and nerves with care. ECA were ligated with ligature and ICA (Internal Carotid Artery) and pterygopalatine artery were also isolated and ligated in similar manner to above procedure then block CCA and ICA using clip. ECA was partially excised with microscissor and the blood vessel was pored to insert probe. The probe was made by the step consisting that 23 mm of 4-0 nylon thread was coated with silicone component such as Polysiloxan solidified with activator to increase their adhesive force to blood vessel. ECA was ligated at the point that about 20 mm of coated probe was inserted to reach at 20 mm or the less from the inserting point and the resistance was felt. The probe was fixed at the same time preventing regurgitation. The skin excision area was sealed again and the rat was restored from anesthetized status naturally. Since inserted probe obstruct the blood flow of MCA, the regional ischemia was induced and the rat was re-anesthetized to remove the probe restoring carotid blood flow after 2 hour. 24 hours after reperfusion, the rat was killed to cervical dislocation to deliver brain and the brain tissue was examined by microscope sectioned 2 mm thickness then stained by 2% TTC solution.

The body temperature was monitored and maintained at 37±0.5° C.

The area of +5.2, +3.2, +1.2, −0.8, −2.8, −4.8, −6.8, −8.8 mm caudal to the Bregma, were excised and terminal tissue was discarded to obtain 6 numbers of brain slices with the thickness of 2 mm using by brain matrix. Optimum amount of 2% triphenyltetrazolium chloride (2,3,5-triphenyltetrazolium-chloride: TTC) solution diluted with distilled water, was poured into 16 well plates. The brain slices were added thereto and stained at 37° C. for 30 minutes. The stained tissues were photographed by digital camera (Olympus Co. c2500L model, USA) and the images were transferred to computer. The volume of cerebral infarction region was calculated by the OPTIMAS program (Media Cybernetics Co., 6.51 version) and analyzed by image analysis system. To determine the exact volume of cerebral infarction region of right hemisphere excluding edema volume (A), the real volume of cerebral infarction (B) was calculated by following Empirical Formula 1 and 2.

$$\text{Correlated infarct volume (mm}^3\text{)} = \text{(total volume (mm}^3\text{)} \text{ of none damaged hemisphere (left)} - \text{(intact volume (mm}^3\text{) of damaged hemisphere (right))} \quad \text{MathFigure 1}$$

$$\text{The infract volume (\%)} = \text{correlated infarct volume (mm}^3\text{)/total volume (mm}^3\text{) of none damaged hemisphere (left)} \times 100 \quad \text{MathFigure 2}$$

At the result, test group treated with various oleic acid (B: 1 mg/kg, C: 10 mg/kg, D: 100 mg/kg) showed smaller staining area with TTC (white) due to little damage of neuronal cell than control group as can be seen in FIG. 1. As shown in FIG. 2, the volume percentage of total infarct hemisphere tissue of control group showed 37.1 4.34%. In a while, the test group C and D showed more potent protective effect on neuronal cell death than control group by 32.9% (20.9 3.48%) and 64.9% (13.0 2.79%) respectively in a dose-dependent manner.

Experimental Example 2

The Neurological Recovery Effect

The neurological recovery activity of oleic acid, was confirmed by neurological score method disclosed in the literature (*Stroke*, 20 pp 84-91, 1989) as follows:

The recovery score was counted by following standard in case the white rat was lifted to about 50 cm higher from the bottom: the fore-rat paw were directed toward the bottom (score 5): the injured rat paw were bounded and without other symptom (score 4); the paw were completely bounded (score 3); the paw were twitched to the left (score 2); and the rat was turned to the left (score 1). The final neurological score of respective group was calculated by summing up total score of respective group in accordance with the above-described evaluation method as shown in FIG. 3. The test group intraperitoneally treated with 100 mg/kg of oleic acid showed higher score (3.95 0.15%; p<0.001) than control group (2.86 0.21).

Experimental Example 3

Toxicity Test

Methods (1)

The acute toxicity tests on ICR mice (mean body weight 25±5 g) and Sprague-Dawley rats (300±10 g, Jung-Ang Lab Animal Inc.) were performed using the oleic acid of the Example 1. Four group consisting of 10 mice or rats was administrated orally with 100 mg/kg, 250 mg/kg, 500 mg/kg and 1000 mg/kg of test sample or solvents (0.2☐, i.p.) respectively and observed for 2 weeks.

Methods (2)

The acute toxicity tests on ICR mice and Sprague-Dawley rats were performed using the extract of the Example 1. Four group consisting of 10 mice or rats was administrated intraperitoneally with 25 mg/kg, 50 mg/kg, 100 mg/kg and 200 mg/kg of test sample or solvents (0.2☐, i.p.), respectively and observed for 24 hours.

Results

There were no treatment-related effects on mortality, clinical signs, body weight changes and gross findings in any group or either gender. These results suggested that the extract prepared in the present invention were potent and safe.

INDUSTRIAL APPLICABILITY

The composition comprising oleic acid according to the present invention shows protective effect of neuronal cell and preventing or treating effect of brain stroke and cerebral ischemia. Therefore, it is useful in the prevention or treatment of degenerative brain diseases in human or mammal.

The invention claimed is:

1. A method of treating brain stroke or cerebral ischemia that is caused by neuronal cell injury from focal cerebral ischemia comprising administering an effective amount of an oleic acid of Formula (I):

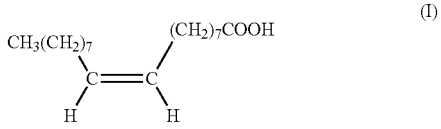

to a mammal in need thereof.

2. The method of claim 1, wherein the mammal is a human.

* * * * *